United States Patent [19]

Hitzeman et al.

[11] Patent Number: 4,803,164

[45] Date of Patent: Feb. 7, 1989

[54] PREPARATION OF HEPATITIS B SURFACE ANTIGEN IN YEAST

[75] Inventors: Ronald A. Hitzeman, Pacifica; Arthur D. Levinson, Burlingame; Daniel G. Yansura, San Francisco, all of Calif.

[73] Assignee: Genentech, Inc., South San Francisco, Calif.

[21] Appl. No.: 42,604

[22] Filed: Apr. 22, 1987

Related U.S. Application Data

[63] Continuation of Ser. No. 599,387, Apr. 12, 1984, abandoned, which is a continuation of Ser. No. 298,236, Aug. 31, 1981, abandoned.

[51] Int. Cl.$^4$ ............... C12P 21/00; C12P 21/02; C12P 21/04; C12N 15/00
[52] U.S. Cl. ..................... 435/68; 435/70; 435/71; 435/172.1; 435/172.3; 435/255; 435/256; 435/320; 536/27; 935/12; 935/37; 935/61; 935/69
[58] Field of Search ............. 435/68, 70, 71, 91, 435/172.1, 172.3, 253, 255, 256, 317.1, 320; 536/27; 935/11, 12, 34, 37, 61, 69

[56] References Cited

FOREIGN PATENT DOCUMENTS

| | | | |
|---|---|---|---|
| 11562 | 5/1980 | European Pat. Off. | 435/172.3 |
| 13828 | 8/1980 | European Pat. Off. | 435/172.3 |
| 20251 | 12/1980 | European Pat. Off. | 435/172.3 |
| 2270892 | 12/1975 | France . | |
| 2034323 | 6/1980 | United Kingdom | 435/172.3 |
| 2068969 | 8/1981 | United Kingdom . | |

PUBLICATIONS

American Type Culture Collection Catalogue of Strains I, Fifteenth Edition, 1982, pp. 480–493.
Genetic Maps, 1984, S. J. O'Brien (ed.), pp. 92–98. Cold Spring Harbor Laboratory, Cold Spring Harbor, N.Y.
Kolata, "Trying to Crack the Second Half of the Genetic Code", Science 233:1037 (1986).
Fraser et al., "Synthesis of Chicken Ovalbumin in Saccharomyses Cerevisiae", in *Microbiology*-1981, Schlessinger (ed.), 1981, American Society for Microbiology, Washington, D.C., pp. 392–395.
Struhl et al., "High–Frequency Transformation of Yeast: Autonomous Replication of Hybrid DNA Molecules", Proc. Natl. Acad. Sci. U.S.A. 76:1035 (1979).
Beggs et al., "Abnormal Expression of Chromosomal Rabbit Beta–Globin Gene in Saccharomyces Cerevisiae", Nature 283:835 (1980).
Hitzeman et al., "Isolation and Characterization of the Yeast 3-Phosphoglycerokinase Gene (PGK) by an Immunological Screening Technique", Proc. Natl. Acad. Sci. U.S.A. 255:12073 (1980).
Hitzeman et al., J. Biol. Chem. 255 (24):12073–12080 (1980).
Broach et al., Gene 8:121–133 (1979).
Valenzuela et al., Nature 280:815–819 (1979).
Charnay et al., PNAS U.S.A. 76 (5):2222–2226 (1979).
Feitelson et al., "Virology" 130: 76–90 (1983).
Mackay et al., "Proc. Natl. Acad. Sci. U.S.A." 78 (7): 4510–4514, (Jul. 1981).
Burrell et al., "Nature" 279: 43–47 (May 1979).
Dubois et al., "Proc. Natl. Acad. Sci. U.S.A." 77(8): 4549–4553 (Aug. 1980).
Moriarty et al., "Proc. Natl. Acad. Sci. U.S.A." 78(4): 2606–2610 (Apr. 1981).
Pasek et al., "Nature" 282: 575–579 (Dec. 1979).
Mercereau–Puijalon et al., "Expression of Eukaryotic Viral and Cellular Genes", Pettersson et al., Ed., 295–303 (1981).
Mercereau–Puijalon et al., "Gene" 11: 163–167 (1980).

*Primary Examiner*—James Martinell

[57] ABSTRACT

Hepatitis surface antigen is synthesized in recombinant yeast hosts transformed with vectors encoding hepatitis surface antigen, preferably under the control of the yeast PGK promoter and preferably in the absence of DNA encoding the surface antigen precursor. Hepatitis surface antigen is assembled by yeast into antigenic 22 nm particles even though hepatitis surface antigen bacterial transformants were not known to be capable of assembling the surface antigen into 22 nm particles.

11 Claims, 8 Drawing Sheets

THE INSERTION OF AN EcoRI SITE IN THE 5' FLANKING DNA OF THE 3-PHOSPHOGLYCERATE GENE OF YEAST

DNA SEQUENCE OF THE 5' END
OF THE YEAST 3-PHOSPHOGLYCERATE KINASE
STRUCTURAL GENE AND FLANKING DNA

```
        -40        -30        -20        -10        -1  MET SER LEU SER SER LYS LEU LEU VAL
5'---------GATCATAAGGAAGTAATTATCTACTTTTTACAACAAATATAAAACA ATG TCT TTA TCT TCA AAG TTG CTC GTC
```

FIG. 2

PREPARATION OF HEPATITIS B SURFACE ANTIGEN IN YEAST

This application is a continuation of application Ser. No. 599,387 filed Apr. 12, 1984, now abandoned which is a continuation of application Ser. No. 298,236 filed Aug. 31, 1981, now abandoned.

FIELD OF THE INVENTION

This invention relates to the use of recombinant DNA technology for the production of hepatitis B surface antigen (HBsAg) in yeast organisms for use in the preparation of vaccines against hepatitis B virus (HBV). In one aspect, the present invention relates to the construction of microbial expression vehicles containing DNA sequences encoding hepatitis B surface protein antigens operably linked to expression effecting promoter systems and to the expression vehicles so constructed. In another aspect, the present invention relates to yeast organisms transformed with such expression vehicles, thus directed in the expression of the DNA sequences referred to above. In yet other aspects, this invention relates to the means and methods of converting the end products of such yeast expression to entities, such as vaccines, useful against hepatitis B virus. In preferred embodiments, this invention provides for particular expression vectors that utilize potent yeast promoters and DNA sequences distal to that encoding the hepatitis B surface antigen protein which, in combination, provide attractive yields of desired protein, produced in particle form of about 22 nm, and containing antigenic determinant(s) of hepatitis B virus.

The publications and other materials hereof used to illuminate the background of the invention, and in particular cases, to provide additional details respecting its practice are incorporated herein by reference, and for convenience, are numerically referenced in the following text and respectively grouped in the appended bibliography.

BACKGROUND OF THE INVENTION

A. Hepatitis B Virus

Hepatitis B (serum hepatitis) virus is transmitted among humans and manifests as chronically debilitating infections which can result progressively in severe liver damage, primary carcinoma and death. In most cases, complete recovery from hepatitis B infections can be expected; however, large segments of the population, especially in many African and Asian countries, are chronic carriers with the dangerous potential of transmitting the disease pandemically.

Hepatitis is caused by a virus vector (hepatitis B virus or HBV) which in its whole state—the so-called Dane particle-represents the virion and consists of a nucleocapsid enclosing a DNA molecule and an envelope surrounding the nucleocapsid. Proteins associated with the virion include the core antigen (HBcAg), a DNA polymerase and the surface antigen (HBsAG) which has been found in serum of infected and carrier humans. Antibodies to HBsAG have also been found in serum HBV infected people. It is believed that HBsAG is the HBV antigen that can induce immunogenic production of antibody (anti-HBs) and thus it would be the principal in an HBV vaccine. Attention is directed to: Dane et al., *Lancet* 1970 (I), 695 (1970); Hollinger et al., *J. Immunology* 107, 1099 (1971); Ling et al., *J. Immunology* 109, 834 (1972); Blumberg, *Science* 197, 17 (1977); Peterson et al., *Proc. Nat. Acad. Sci* (USA) 74, 1530 (1977) and *Viral Hepatitis, A Contemporary Assessment of Etiology, Epidemiology, Pathogenesis and Prevention.* (Vyas et al., eds.) Franklin Institute Press, Philadelphia, 1978, each of which is hereby incorporated by this reference to further illustrate the background of this invention.

HBsAg is present in infected plasma predominantly in the form of spherical particles having diameters ranging from about 16 to 25 nm—the so-called "22 nm particle." These are thought to represent a noninfectious viral envelope. Because antibodies against HBsAg are protective against HBV infection, these non-infectious particles can effectively be used as a vaccine.

Inasmuch as the hepatitis B virus has not been infectious in cell culture and can only be obtained from infected humans or higher primates, means have not been available for obtaining and maintaining sufficient supplies of HBV for use in producing antigen for immunization against HBV.

The present invention provides the means and methods for producing a vaccine effective against HBV. By means of recombinant DNA technology, the gene encoding HBsAg was inserted together with appropriate translational start and stop signals under the control of an appropriate expression promoter into a replicable expression vector and the latter used to transform yeast cells. The cells, thus genetically directed, produced HBsAg directly and in particle form which, when purified, is suitable to immunize against HBV.

B. Recombinant DNA Technology

With the advent of recombinant DNA technology, the controlled microbial production of an enormous variety of useful polypeptides has become possible. Many mammalian polypeptides, such as human growth hormone and leukocyte interferons, have already been produced by various microorganisms. The power of the technology admits the microbial production of an enormous variety of useful polypeptides, putting within reach the microbially directed manufacture of hormones, enzymes, antibodies, and vaccines useful against a wide variety of drug-targeting applications.

A basic element of recombinant DNA technology is the plasmid, an extrachromosomal loop of double-stranded DNA found in bacteria oftentimes in multiple copies per cell. Included in the information encoded in the plasmid DNA is that required to reproduce the plasmid in daughter cells (i.e., a "replicon" or origin of replication) and ordinarily, one or more phenotypic selection characteristics, such as resistance to antibiotics, which permit clones of the host cell containing the plasmid of interest to be recognized and preferentially grown in selective media. The utility of bacterial plasmids lies in the fact that they can be specifically cleaved by one or another restriction endonuclease or "restriction enzyme", each of which recognizes a different site on the plasmid DNA. Thereafter heterologous genes or gene fragments may be inserted into the plasmid by endwise joining at the cleavage site or at reconstructed ends adjacent to the cleavage site. Thus formed are so-called replicable expression vehicles.

DNA recombination is performed outside the microorganism, and the resulting "recombinant" replicable expression vehicle, or plasmid, can be introduced into microorganisms by a process known as transformation and large quantities of the recombinant vehicle obtained by growing the transformant. Moreover, when the gene is properly inserted with reference to portions of the plasmid which govern the transcription and translation of the encoded DNA message, the resulting expression vehicle can be used to direct the production of the polypeptide sequence for which the inserted gene codes, a process referred to as expression.

Expression is initiated in a DNA region known as the promoter. In the transcription phase of expression, the DNA unwinds exposing it as a template for initiated synthesis of messenger RNA from the DNA sequence. The messenger RNA is, in turn, bound by ribosomes, where the messenger RNA is translated into a polypeptide chain having the amino acid sequence encoded by the mRNA. Each amino acid is encoded by a nucleotide triplet or "codon" which collectively make up the "structural gene", i.e., that part of the DNA Sequence which encodes the amino acid sequence of the expressed polypeptide product. Translation is initiated at a "start" signal (ordinarily ATG, which in the resulting messenger RNA becomes AUG). So-called stop codons define the end of translation and, hence, the production of further amino acid units. The resulting product may be obtained by lysing the host cell and recovering the product by appropriate purification from other bacterial proteins.

In practice, the use of recombinant DNA technology can express entirely heterologous (not ordinarily found in, or produced by, a given micro-organism), polypeptides—so-called direct expression—or alternatively may express a heterologous polypeptide fused to a portion of the amino acid sequence of a homologous (found in, or produced by, the corresponding wild-type microorganism) polypeptide. In the latter cases, the intended bioactive product is sometimes rendered bioinactive within the fused, homologous/heterologous polypeptide until it is cleaved in an extracellular environment. See, eg., British Pat. Publ. No. 2 007 676 A and Wetzel, *American Scientist* 68, 664, (1980).

If recombinant DNA technology is to fully sustain its promise, systems must be devised which optimize expression of gene inserts, so that the intended polypeptide products can be made available in controlled environments and in high yields.

C. State of the Art

British patent application No. 2034323A, published June 4, 1980, describes the isolation of the HBV genome comprising about 3200 nucleotides and the incorporation of this DNA into a vector taking advantage of an EcoRI digest and subsequent ligation. It is stated that the resultant cloned HBV-DNA can be labelled and used as a probe to detect Dane particles in serum and that the vector could be used to express a polypeptide containing a hepatitis B protein fragment.

In a related article from the same laboratories (*Proc. Natl. Acad. Sci* (USA) 77, 4549 (1980)), it is reported that tandem cloned heptatis B genomes were introduced into mouse cells and integrated into the mouse chromosome. Polypeptide identified as hepatitis surface antigen was excreted from the cells as particles similar to those found in the sera of infected humans.

European patent application Publication No. 13828 describes the production of HBV core antigen by readthrough translation of an mRNA transcript from the genomic DNA. No surface antigen was detected.

In European patent applications Publication No. 20251 there is described the production in *E. coli* of a fusion protein purportedly containing a portion of the surface antigen protein of HBV. Because the surface antigen determinants were present as a fusion protein, the structure could not be native; hence, the reported low immunological activity.

SUMMARY OF THE INVENTION

The present invention is based upon the discovery that recombinant DNA technology can be used to successfully and efficiently produce the hepatitis B surface antigens, directly and in discrete particle form. The product is suitable for use in conferring immunogenicity to hepatitis B virus in a susceptible human or for preparing a vaccine for such use. The product is produced in a eukaryotic host—yeast—and thus carries the advantages such systems confer on corresponding, proteinaceous products, to wit, glycosylation and sugar and lipid association more closely related to human produced proteins versus bacterial produced proteins whose hosts are incapable of such sophisticated processing. In addition, the eukaryotic yeast cells tolerate the protein product better than prokaryotic systems, doubtless increasing expression levels and yields significantly over bacterial systems, in which the hepatitis protein per se proved lethal.

The present invention comprises the hepatitis B surface antigen (HBsAG) produced and the methods and means of its production. Specifically, the present invention is directed to HBsAg in particle form comprising immunogenic determinant(s) of hepatitis B virus, produced in yeast. The HBsAg hereof is produced in discrete particle form, devoid of any additional, fused polypeptide artifact, whether encoded by another portion of the HBV genome or by DNA homologous to the yeast strain employed. The present invention is further directed to replicable DNA expression vehicles harboring gene sequences encoding HBsAg in directly expressible form. Further, the present invention is directed to yeast strains transformed with the expression vehicles described above and to microbial cultures of such transformed yeast strains, capable of producing HBsAg. In still further aspects, the present invention is directed to various processes useful in preparing said HBsAg gene sequences, DNA expression vehicles, yeast strains and cultures and to specific embodiments thereof. Still further, this invention is directed to the use of thus produced HBsAg for the preparation of vaccines useful to confer immunogenicity to HBV in susceptible humans, to such vaccines and to the method of using them to inoculate and confer immunogenicity to HBV in susceptible humans.

DESCRIPTION OF PREFERRED EMBODIMENTS

The preferred promoter herein is one tailored from the yeast 3-phosphoglycerate kinase (PGK) promoter region which is described infra. The PGK gene was analyzed for restriction sites which would be useful for sequencing. DNA sequence analysis around one of these restriction sites indicated that translation beginning with a specific ATG would yield a protein whose N-terminal amino acids corresponded to the same N-terminal amino acids of human and horse PGK, this flanking DNA being considered the yeast PGK promoter region. The PGK promoter region was analyzed for a region which would logically support a unique restriction site. A primer repair reaction was carried out and this unique site was placed at the 3' end of the 2GK promoter region. This unique site allowed the PGK promoter region to effect the direct expression of the thus fused gene in yeast.

A yeast/bacteria shuttle plasmid, pCV13 (or YEp13) described infra, had certain restriction fragments removed. Replacement of these fragments by PGK promoter region fused to surface antigen allowed reclosure of the vector. This vector was used to transform yeast which were grown up under customary fermentation conditions and permitted to produce the desired HBsAg product. Recovery of product followed by breaking open the transformed yeast. Supernatants from centrifuged solution were used as a substrate in hepatitis B surface antigen radioimmune assays.

A particular DNA sequence, found to be suitable herein as a transcription terminator, was placed after the gene sequence encoding HBsAg in order to terminate mRNA synthesis and provide a Poly A addition site for proper mRNA processing and translation. This terminator is based upon the 232 bp Hind III-to-BglII restriction fragment from the Trp1 gene contained in pFRL4. This fragment was isolated containing some coding sequence from the yeast TRP1 gene and the 3'-flanking sequence required for proper transcription termination and polyadenylation. This terminator fragment was fused via its HindIII site to the HindIII site of the HBsAg gene. Transcription of the HBsAg gene by a fused yeast promoter in yeast is designed to terminate in the fused TRP1 terminator fragment.

pCV13(1) contains the ampicillin and tetraycline resistance genes allowing for plasmid selection in E. coli, an E. coli origin of DNA replication, the LEU2 gene allowing for selection of the plasmid in yeast and the 2 (micron) origin allowing for DNA replication of the plasmid in yeast. This plasmid is found in the nucleoplasm of transformed yeast. The small HindIII-to-BamHI fragment from the tetracycline resistance gene was removed from the vector. The resulting large vector fragment was then ligated with the 1.6 kbp HindIII-to-EcoRI assembled PGK promoter fragment and a 1.1 kbp EcoRI-to-BglII HBsAg/TRP1 terminator fragment so as to produce the pYcHBs vector in FIG. 6. This HBsAg expression vector was constructed to have the PGK promoter fragment initiate transcription of the HBsAg structural gene and then terminate this transcript in the TRP1 terminator previously fused to the HBsAg gene.

BRIEF DESCRIPTION OF THE DRAWINGS

FIG. 2 illustrates the 5'-flanking sequence plus the initial coding sequence for the PGK gene before insertion of an XbaI and EcoRI sites.

YEAST HOST ORGANISMS

Figure 1:
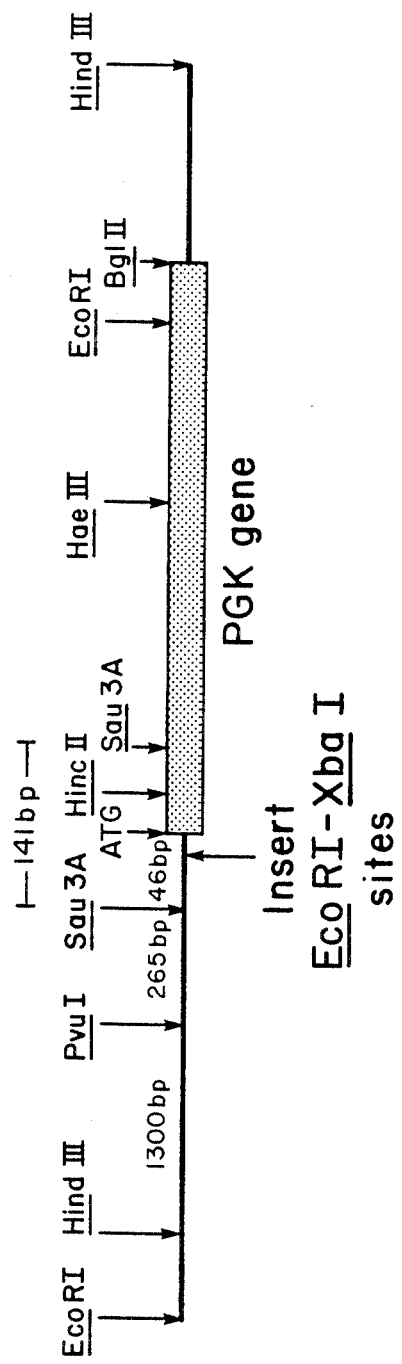
FIG. 1 schematically illustrates the restriction map of the 3.1 kbp HindIII insert of vector pB1 from which the PGK promoter was isolated. Indicated is the insertion of an EcoRI site and an XbaI site in the 5'-flanking DNA of the PGK gene.

In the preferred embodiments hereof, the expression system was placed in the plasmid pCV13 (1), which is capable of selection and replication in both E. coli and yeast, Saccharomyces cerevisiae. For selection in yeast the plasmid contains the LEU2 gene (2) which complements yeast (allows for growth in the absence of leucine) containing mutations in this gene found in chromosomes III of yeast (3). The strain used here was the strain XV610-8C which has the genotype a leu2 trp1 ade6 ade2 lys1 can1. This strain is being deposited in the American Type Culture Collection, 12301 Park Lawn Drive, Rockville, Md. 20852 without restriction concurrently with the filing of the present application (ATCC No. 20622). However, it will be understood that any Saccharomyces cerevisiae strain containing a mutation which makes the cell Leu2 should be an effective environment for expression of the plasmid containing the expression system. An example of another strain which could be used is ATCC No. 38626 which has the genotype, a leu2-3 leu2-112 his4-519 can1 (4). This strain has two point mutations in leu2 which restricts reversion and allows for tighter transformation of Leu− to Leu+.

Yeast Promoters

The 5'-flanking DNA sequence from a yeast gene (for alcohol dehydrogenase 1) can promote the expression of a foreign gene (eg. leukocyte interferon D) when placed in a plasmid used to transform yeast. Another yeast gene has been placed at the 3'-end of this construction to allow for proper transcription termination and polyadenylation in yeast. Indeed, we have shown that the mRNA transcript does end (3'-end) as expected in the termination/adenylation region of the yeast TRP1 gene (Hitzeman et. al., Nature, in press). This promoter can be suitably employed in the present invention as well as others—cf. infra. In the preferred embodiment, the 5'-flanking sequence of the yeast 3-phosphoglycerate kinase gene (5) was placed upstream from the structural sequence for hepatitis surface antigen followed again by DNA containing the TRP1 gene termination-polyadenylation signals.

Since both the yeast alcohol dehydrogenase I 5' flanking sequence and the 3-phosphoglycerate kinase 5'-flanking sequence (infra) can function to promote expression of foreign genes in yeast, it seems likely that the 5'-flanking sequences of any highly-expressed yeast gene could be used for the expression of important gene products. Since under some circumstances yeast expressed up to 65 percent of its soluble protein as glycolytic enzymes (6) and since this high level appears to result from the production of high levels of the individual mRNAs (7), it should be possible to use the 5'-flanking sequences of any other glycolytic genes for such expression purposes—e.g., enolase, glyceraldehyde—3-phosphate dehydrogenase, hexokinase, puruvate decarboxylase, phosphofructokinase, glucose-6-phosphate, isomerase, 3-phosphoglycerate mutase, pyruvate kinase, triosephosphate isomerase, phosphoglucose isomerase, and glucokinase. Any of the 3'-flanking sequences of these genes could also be used for proper termination and mRNA polyadenylation in such an expression system-cf. Supra. Some other highly expressed genes are those for the acid phosphatases (8) and those that express high levels of production due to mutations in the 5'-flanking regions (mutants that increase expression-)—usually due to the presence of a Tyl transposon element (9).

All of the genes mentioned above are thought to be transcribed by yeast RNA polymerase II (9). It is possible that the promoters for RNA polymerase I and III which transcribe ribosomal DNA, 5S DNA, and tRNA DNA (9, 10), may also be useful in such expression constructions.

Finally, many yeast promoters also contain transcriptional control so that they can be turned off or on by variation in growth conditions. Some examples of such yeast promoters are the genes that produce the following proteins: Alcohol dehydrogenase II, isocytochrome, acid phosphatase, degradative enzymes associated with nitrogen metabolism, glyceraldehyde-3-phosphate dehydrogenase, and enzymes responsible for maltose and galactose utilization (9). Such a control region would be very useful in controlling expression of protein product—especially when their production is toxic to yeast. It should also be possible to put the control region of one 5'-flanking sequence with a 5'-flanking sequence containing a promoter from a highly expressed gene. This would result in a hybrid promoter and should be possible since the control region and the promoter appear to be physically distinct DNA sequences.

DETAILED DESCRIPTION

Identification of PGK Promoter DNA

The six N-terminal amino acids of the 3-phosphoglycerate enzyme purified from humans are as follows:

```
  1  -  2  -  3  -  4  -  5  -  6
SER—LEU—SER—HSM—LYS—LEU—
```

One of the translational reading frames generated from the DNA sequence of the 141 bp Sau3A-to-Sau3A restriction fragment (containing the internal HincII site; see PGK restriction map (FIG. 1) produces the following amino acid sequence.

```
  1  -  2  -  3  -  4  -  5  -  6
MET—SER—LEU—SER—SER—LYS—LEU—
```

After removal of initiator methionine, it is seen that PGK N-terminal amino acid sequence has 5 of 6 amino acid homology with N-terminal amino acid sequence of human PGK.

This sequencing result suggested that the start of the yeast PGK structural gene is coded for by DNA in the 141 bp Sau3A restriction fragment of pB1. Previous work (5) has suggested that the DNA sequences specifying the PGK mRNA may reside in this area of the HindIII fragment. Further sequencing of the 141 bp Sau3A fragment gives more DNA sequence of the PGK promoter (Shown in FIG. 2).

Figure 3:
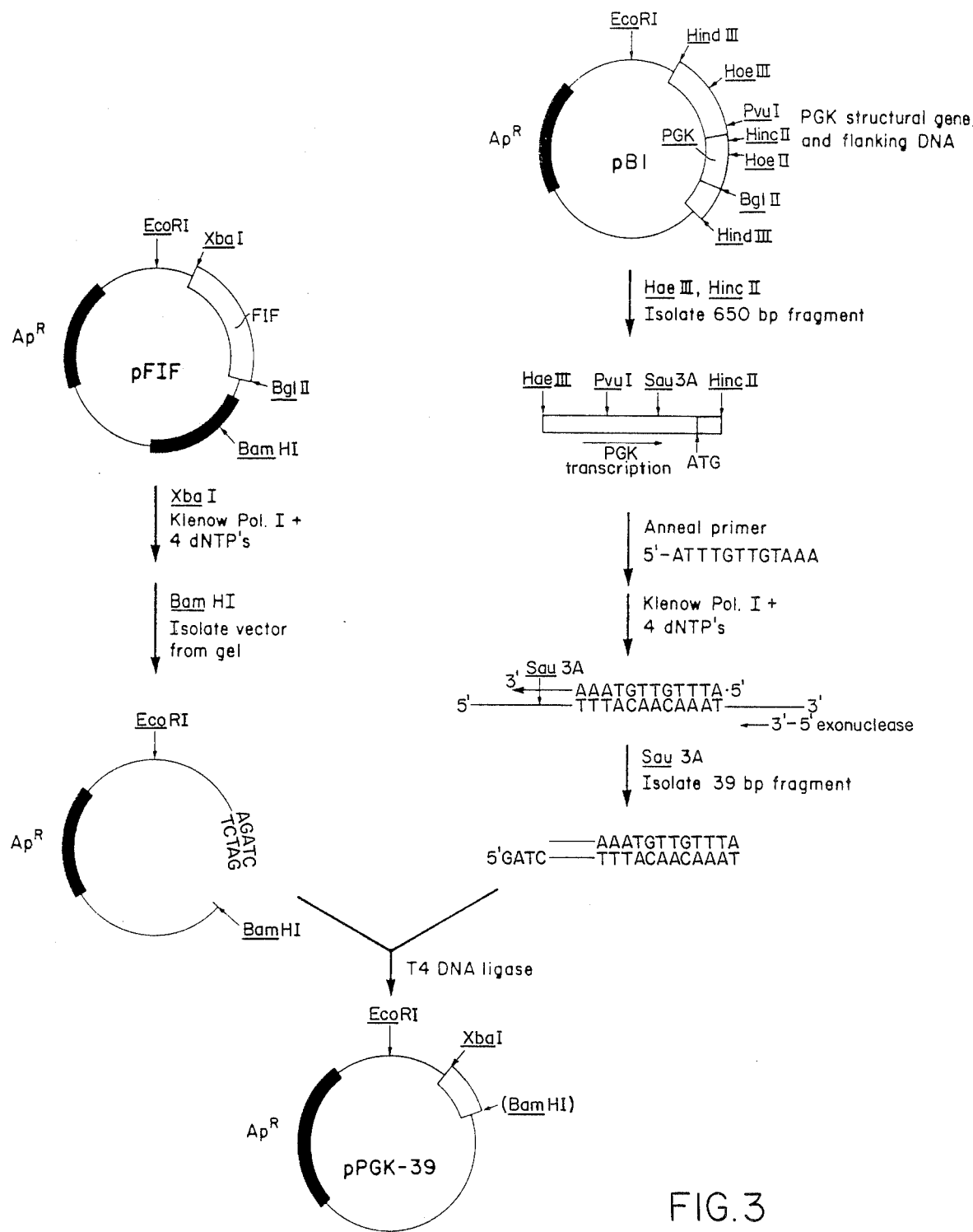
FIG. 3 schematically illustrates techniques used to insert an XbaI site at position-8 in the PGK promoter and to isolate a 39 bp fragment of the 5'-flanking sequence of PGK containing this XbaI end and a Sau3A end.

Protocol: For the insertion of XbaI/EcoRI sites in the 5'-flanking sequence of the PGK gene and the Construction of a Promoter Fragment (see FIG. 1):

Step (1) Primer-repair reaction and cloning of 39 bp XbaI=to Sau3A fragment (as shown in FIG. 3).

Figure 4:
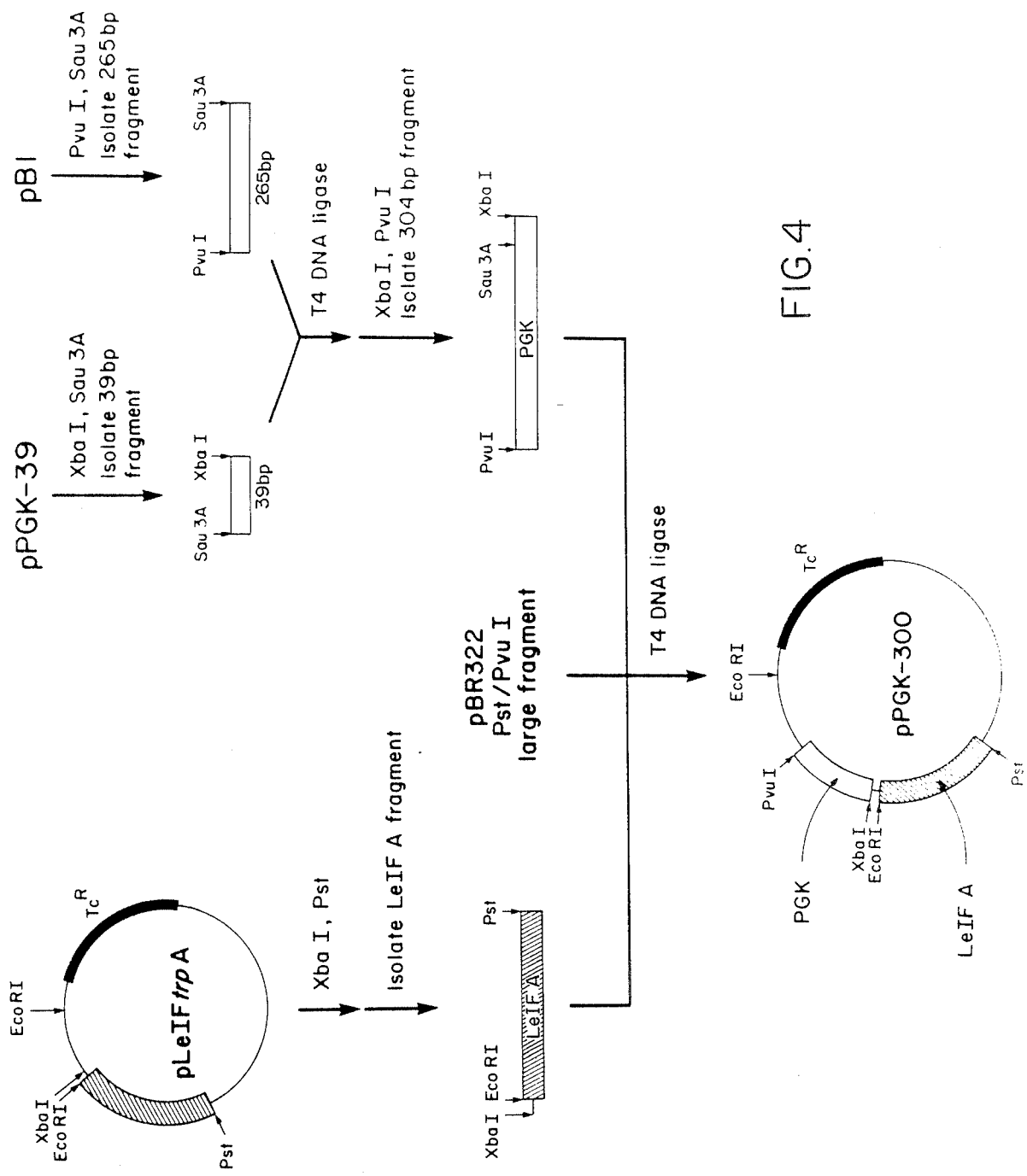
FIG. 4 schematically illustrates the construction of a 300 bp fragment containing the above 39 bp fragment, additional PGK 5'-flanking sequence (265 bp) from PvuI to Sau3A (see FIG. 1), and a EcoRI site adjacent to XbaI.

Step (2) Clone PvuI-to-XbaI partial promoter fragment (as shown in FIG. 4).

Figure 5:
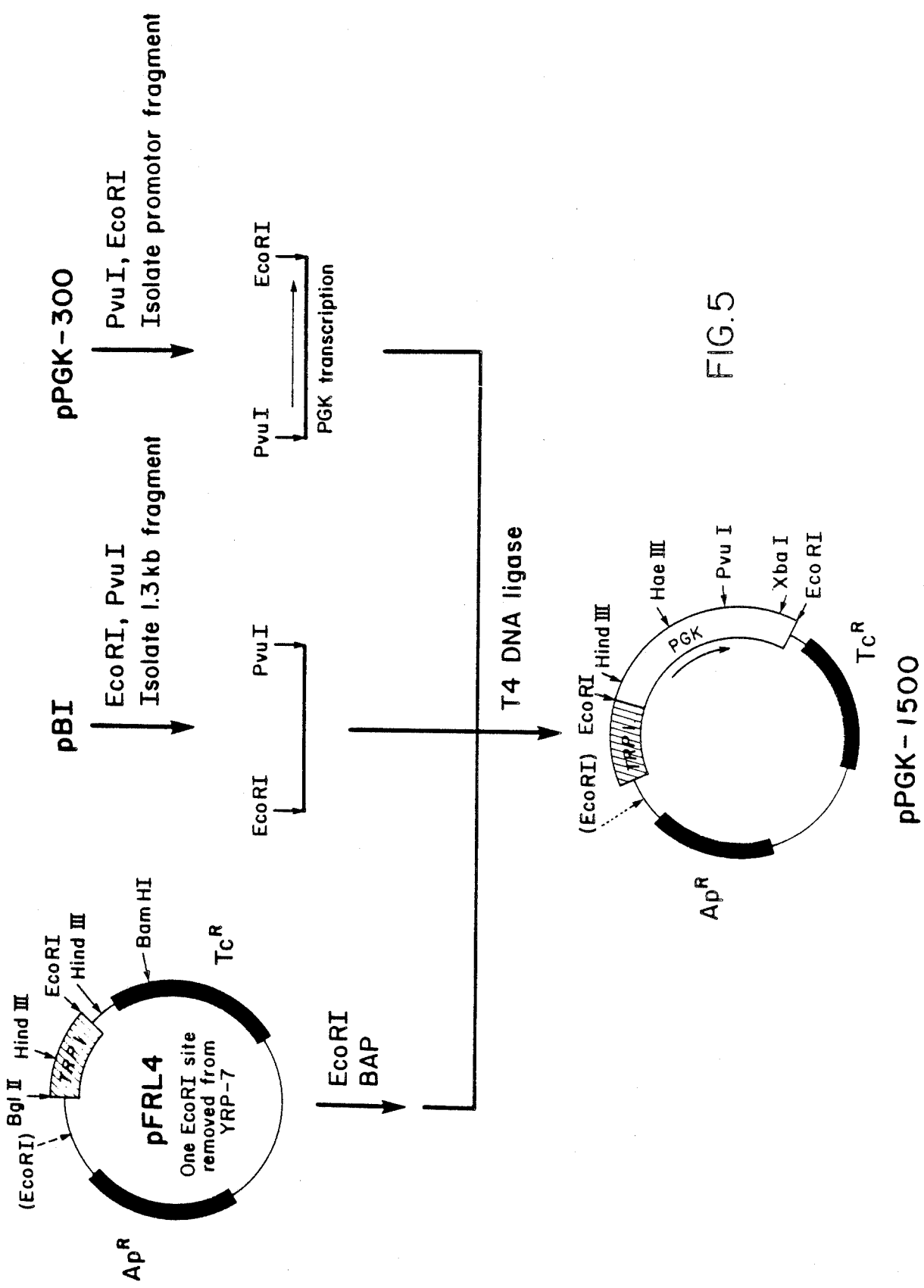
FIG. 5 schematically illustrates the construction of the 1500 bp PGK promoter fragment (HindIII/EcoRI) which contains, in addition to the fragment constructed in FIG. 4, a 1300 bp HindIII to PvuI fragment from PGK 5'-flanking sequence (see FIG. 1).
Figure 6:
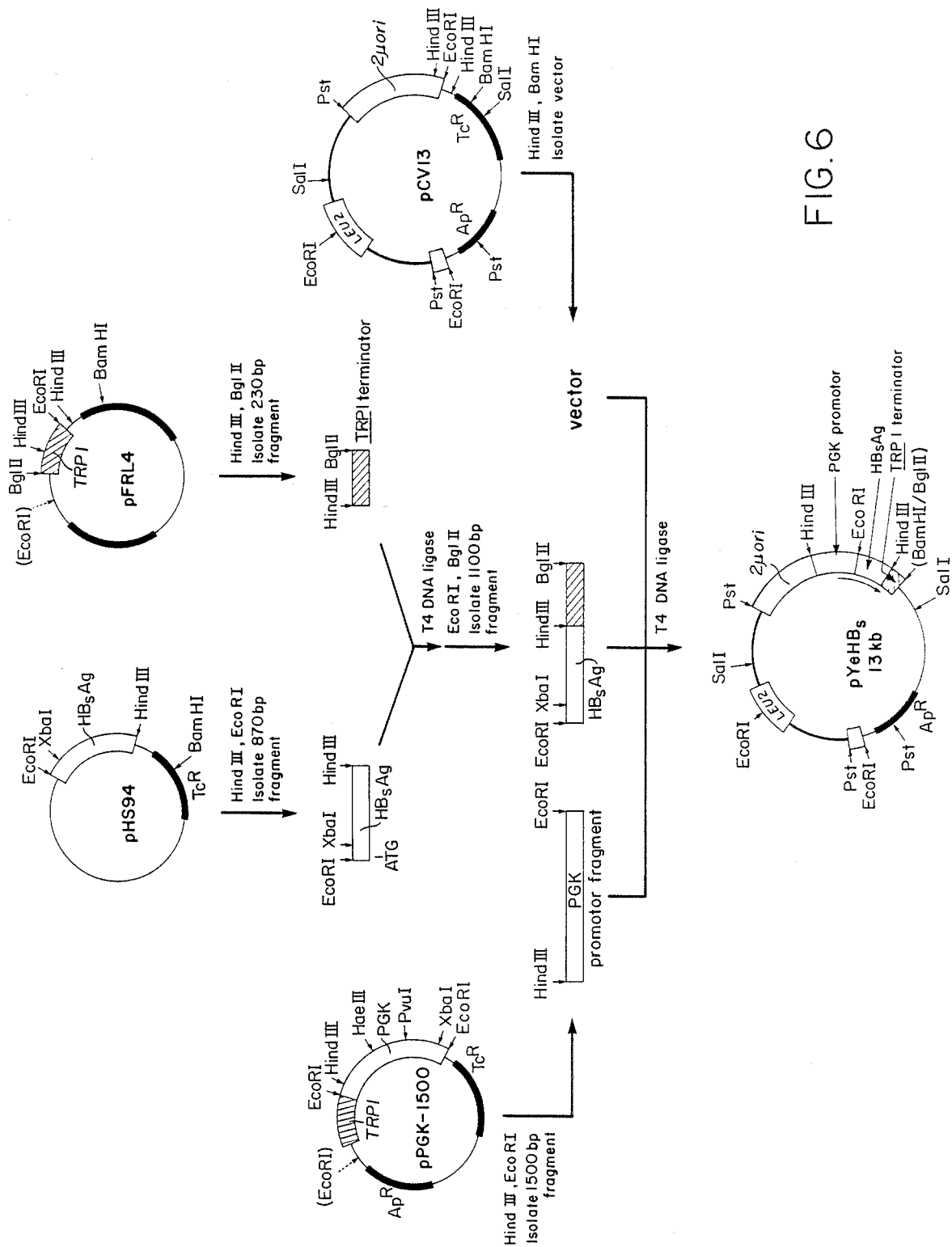
FIG. 6 schematically illustrates the construction of an expression vector for hepatitis surface antigen in yeast, containing the modified PGK promoter, the HBsAg gene, and the terminator region of the yeast TRP1 gene, as described in more detail herein.

Step (3) Clone EcoRI-to-EcoRI promoter fragment (as shown in FIG. 5)-contains the HindIII-to-EcoRI promoter fragment used in FIG. 6 for construction of expression plasmid.

Insertion of EcoRI Restriction Site In the PGK Promoter and Promoter Reassembly

The use of the PGK promoter for direct expression of heterologous genes in yeast requires that there be a restriction site on the 3' end of the PGK promoter fragment which does not contain the PGK initiator ATG. FIGS. 1, 3, 4 and 5 show how we inserted an EcoRI site in the PGK promoter. We used a primer-repair reaction (11) to first insert an XbaI site in the 3' end of promoter sequence. This XbaI sticky end was ligated to the XbaI site of a LEIFA (12) gene containing an EcoRI site adjacent to the Xba1 site. This connection sequence at the 5' end of the LEIFA gene is as follows:

5'-TCTAGAATTCATG-3'
3'-AGATCTTAAGTAC-5'

This connection on the LEIFA gene is how an EcoRI site was inserted next to the XbaI site on the PGK promoter. Use of this XbaI-to-EcoRI connection allows for placement of structural genes containing either of these restriction ends at the 3' end of the PGK promoter for expression purposes.

Construction of expression vector

Isolation of HBsAg Structural Gene

The structural gene coding for the HBsaAg was recovered from a plasmid (pHBV-7-1A) containing the entire genome of HBV cloned into the EcoRI site of pBR322. This clone was obtained by methods similar to those recently published by Valenzuela et. al. (14) and (15).

The structural gene was modified in two ways (1) to incorporate a unique restriction site directly in front of the initial ATG methionine codon and (2) to blunt-end ligate the HBV Hpa I site located distal to the HBsAg gene to the filled in EcoRI site of pBR322. These two modifications to the DNA fragment containing the HBsAg structural gene were accomplished as described below:

(1.) 50 μg of pHBV-T-IA DNA was first digested with Hpa II (80 units) in 200 μl reaction mixture according to enzyme supplier's (BRL) reaction condition to obtain a 1.7 kb DNA fragment, in which the initiation codon for the coding sequences of HBsAg was located close to the 5' end of the sense-strand (about 400 bp). The DNA was purified by electrophoresis on polyacrylamide gels. (PAGE). The purified HpaII fragment was then treated with λ exonuclease (2 units) in 100 μl reaction mixture (New England BioLab) for 30 minutes at 37° C. λ exonuclease is a 5' exonuclease which digests double stranded DNA. This reaction degraded the 5' half of the "sense-strand" DNA from HBsAg coding sequences and exposed the antisense strand for pairing with added primer. The λ exonuclease treated DNA was deproteinized and resuspended in 50 μl of reaction mixture containing 40 mM potassium phosphate buffer (pH 7.4), 1 mM DTT, 50 μg/ml BSA, 6 mM MgCl2, 0.5 mM each of dNTPs, and 0.2 n mole of dATG-GAGAACATC ($^{32}$P-labelled at 5' end by polynucleotide kinase). The mixture was first heated at 90° C. for 1 minute, annealed at 0° C. for 30 minutes and then incubated at 37° C. for 3 hours in the presence of 2 units of E. coli DNA polymerase I Klenow fragment (16). The DNA polymerase synthesized DNA primed by the added primer and degraded single-stranded DNA with 3'-OH termini and, therefore, created blunt ended DNA molecules. The resultant DNA was then deproteinized, digested with XbaI (45 units) at a site located within the HBsAg gene in a 100 μl reaction mixture and fractionated by PAGE. A 91 base pair DNA fragment containing the first 30 codons of HBsAg gene was isolated after autoradiographic detection (fragment A).

To create a unique restriction site site immediately 5' to the HBsAg gene, we took advantage of a derivative of the plasmid pBR322 (called pNCV) which contains a synthetic DNA segment with the sequence:
AATTCTGCAG
GACGTCTTAA
located at the EcoRI site. Incorporated into this synthetic DNA sequence is a PstI site. Ten μg of pNCV DNA was first cut with 24 units of PstI enzyme in a 100 μl reaction mixture and then treated with 2 units E. coli DNA polymerase Klenow fragment in 50 μl reaction mixture as described above at 8° C. for 1 hour. The DNA polymerase treatment removed the 4 base-pair 3' overhang created by PstI digestion to leave a blunt ended DNA with an intact EcoRI restriction site giving the fragment B, containing the origin of replication of pBR322. The blunt ended HBsAg gene fragment A prepared above was ligated to the EcoRI site of fragment B. This was accomplished in a three fragment ligation to create a plasmid pAS94. The third fragment (fragment C) was prepared as follows:

(2.) The HBsAg gene from the plasmid pHBV-T-1A was cleaved with HpaI at a site distal to the HBsAg gene. The HpaI site was ligated to a EcoRi site of pBR322 previously filled in with DNA polymerase I Klenow fragment (16). This was accomplished by subcloning the derivative of pBR322 to give pAS42. This plasmid was cleaved with XbaI (which cleaves at codon 31) and with Bam HI (which cleaves 375 base pairs from the EcoRI site of pBR322) to give a DNA fragment containing most of the HBsAg gene, ca. 150 base pairs distal to the HBsAg gene, and the promoter/operator and the first 200 base pairs of the tetracycline resistance gene. The DNA fragment C, bounded by XbaI and BamHI was isolated by PAGE and used in the three fragment ligation described above to give the plasmid pHS94. (FIG. A).

Successful expression of a heterologous gene in yeast requires that transcription of that gene end with a sequence of DNA which allows for proper processing (polyadenylation) and transport of that transcript.

DNA RESTRICTION AND MODIFICATION ENZYMES

Restriction enzymes EcoRI and HindIII along with bacterial alkaline phosphatase were purchased from Bethesda Research Laboratories. DNA polymerase (Klenow fragment) was purchased for Boehringer-Mannheim. T4 polynucleotide kinase, ATP and the deoxynucleoside triphosphates dATP, dGTP, dCTP and dTTP were purchased from PL Biochemicals. All other DNA restriction and metabolic enzymes were purchased from New England Biolabs. [γ-$^{32}$P]ATP was purchased from Amersham Corp. DNA restriction and metabolic enzymes were used in conditions exactly described by their respective manufacturers.

DNA Preparation and Transformation

Purification of covalently closed circular plasmid DNAs from E. coli (17) and yeast (18) plus the transformation of E. coli (19) and yeast (20, 21) were performed as previously described. E. coli miniscreens were done as previously described (22).

Strains and Media

E. coli K-12 strain (ATCC No. 31446) (23) was used for all bacterial transformations. Yeast strain XV610-8C having the genotype (leu2 trp1 ade6 and/or ade2, lys1 can1 was used as yeast cloning host. (ATCC No. 20622).

LB (rich) medium was prepared as described by Miller (24) with the addition of either 20 μg/ml ampicillin (Sigma) or 20 μg/ml tetracycline (Sigma).

Restriction Map and Partial Sequencing of 3.1 kb Insert of pB1

300 μg of pB1(5) was exhaustively digested with HindIII in a 500 μl reaction volume, then electrophoresed on a 1 percent agarose preparative agarose (Sea Kem) gel. The 3.1 kb HindIII insert was cut from the ethidium stained gel, electroeluted (25), 2x extracted with equal volumes of buffer-saturated phenol and chloroform before ethanol precipitation. Portions of the resuspended DNA fragment was divided up and subjected to restriction cuts with a group of different restriction enzymes to yield the partial restriction map depicted in FIG. 1.

30 μg of the purified 3.1 kb insert was cut with Sau3A then run on a 6 percent acrylamide gel. Fragments corresponding to the 265 bp and 141 bp were separately purified by electroelution as described above. Each DNA fragment was then subjected to DNA sequence analysis (25).

A portion of this DNA sequence is shown in FIG. 2. Amino acids corresponding to the N-terminal amino acids of the PGK structural gene are printed above the DNA sequence.

Insertion of a Restriction Site in the PGK 5' Promoter Region

A synthetic oligonucleotide with the sequence 5'ATTTGTTGTAAA3' was synthesized by standard methods (26). 100 ng of this primer was labeled at the 5' end using 10 units of T4 polynucleotide kinase in a 20 μl reaction also containing 200 μCi of [γ$^{32}$-P] ATP. This labeled primer solution was used in a primer-repair reaction designed to be the first step in a multi-step process to put an EcoRI restriction site in the PGK 5'-flanking DNA just preceeding PGK structure gene sequence. The multistep process is explained below:

Step 1 (FIG. 3)

Primer repair reactions and cloning of 39 bp XbaI-to-Sau3A PGK piece

100 μg of pB1 was completely digested with HaeIII then run on a 6 percent polyacrylamide gel. The uppermost band on the ethidum stained gel (containing PGK promoter region) was isolated by electroelution as described above. This 1200 bp HaeIII piece of DNA was restricted with HindII then run on a 6 percent acrylamide gel. The 650 bp band was isolated by electroelution, 5 μg of DNA was isolated. This 650 bp HaeIII-to-HindII piece of DNA was resuspended in 20 μl dIH2O, then mixed with the 20 μl of the phosphorylated primer solution described above. This mixture was 1 X phenol-chloroform extracted then ethanol precipitated. Dried DNA was resuspended in 50 μl of H2O and then heated in a boiling water bath for seven minutes. This solution was then quickly chilled in a dry ice-ethanol bath (10–20 seconds) then transferred to an ice-water bath. To this solution was added 50 μl of a solution containing 10 μl of 10 X DNA polymerase I buffer (Boehringer Mannheim), 10 μl of a solution previously made 2.5 mM in each deoxynucleoside triphosphate (dATP, dTTP, dGTP and dCTP), 25 μl of dIH2O and 5 units of DNA Polymerase I, Klenow fragment. This 100 μl reaction was incubated at 37° C. for 4 hours. The solution was then 1 X phenol-chloroform extracted, ethanol precipitated, dried by lyophilization then exhaustively restricted with 10 units of Sau3A. This solution was then run on a 6 percent acrylamide gel. The band corresponding to 39 bp in size was cut from the gel then isolated by electroelution described above. This 39 bp band has one blunt end and one Sau3A sticky end. This fragment was cloned into a modified pFIFtrp69 vector (11). 10 μg of pFIFtrp69 was linearized with XbaI, 1 X phenol chloroform extracted, then ethanol precipitated. The XbaI sticky end was filled in using DNA Polymerase I Klenow fragment in a 50 μl reaction containing 250 μM in each nucleoside triphosphate. This DNA was cut with BamHI then run on a 6 percent acrylamide gel. The vector fragment was isolated from the gel by electroelution then resuspended in 20 μl dIH2O. 20 ng of this vector was ligated with 20 ng of the 39 bp fragment synthesized above for 4 hours at room temperature. One-fifth of the ligation mix was used to transform E. coli strain 294 to ampicillin resistance (on LB +20 μg/ml amp plates. Plasmids from the transformants were examined by a quick screen procedure (22). One plasmid, pPGK-39 (36) was selected for sequence analysis. 20 μg of this plasmid was digested with XbaI, ethanol precipitated then treated with 1000 units of bacterial alkaline phosphatase at 68° C. for 45 min. The DNA was 3 X phenol-chloroform extracted, then ethanol precipitated. The dephosphorylated ends were then labeled in a 20 μl reaction containing 200 μCi of [$\delta^{32}$-P] ATP and 10 units of T4 polynucleotide kinase. The plasmid was cut with SalI and run on a 6 percent acrylamide gel.

The labeled insert band was isolated from the gel and sequenced by the chemical degradation method (25). The DNA sequence at the 3'-end of this promoter piece was as expected.

Step 2 (FIG. 4)

Construction of 312 bp PvuI-to-EcoRI PGK Promoter Fragment

25 μg of pPGK-39 (FIG. 3) was simultaneously digested with SalI and XbaI (5 units each) then electrophoresed on a 6 percent gel. The 390 bp band containing the 39 bp promoter piece was isolated by electroelution. The resuspended DNA was restricted with Sau3A then electrophoresed on an 8 percent acrylamide gel. The 39 bp PGK promoter band was isolated by electroelution. This DNA contained 39 bp of the 5' end of the PGK promoter on a Sau3A-to-XbaI fragment.

25 μg of pB1 was restricted with PvuI and KpnI then electrophoresed on a 6 percent gel. The 0.8 kbp band of DNA was isolated by electroelution, then restricted with Sau3A and electrophoresis on a 6 percent gel. The 265 bp band from the PGK promoter (FIG. 1) was isolated by electroelution.

This DNA was then ligated with the 39 bp promoter fragment from above for two hours at room temperature. The ligation mix was restricted with XbaI and PvuI then electrophoresed on a 6 percent acrylamide gel. The 312 bp Xba-to-PvuI restriction fragment was isolated by electroelution, then added to a ligation mix containing 200 ng of pBR322 [previously isolated missing the 162 PvuI-to-PstI restriction fragment] and 200 ng of the XbaI-to-pst I LeIFA cDNA gene previously isolated from 20 μg of pLEIFtrpA. This 3-factor-ligation mix was used to transform E. coli strain 294 to tetracycline resistance. Transformant clonies were miniscreened and one of the colonies, pPGK-300 was isolated as having 304 bp of PGK 5'-flanking DNA fused to the LeIFA gene in a pBR322 based vector. The 5' end of the LeIFA gene has the following sequence: 5'-CTAGAAATTC 3', thus fusion of the XbaI site from the PGK promoter fragment into this sequence allows for the addition to the XbaI site an EcoRI site. pPGK-300 thus contains part of the PGK promoter isolated in a PvuI-to-EcoRI fragment.

Step 4

Construction of a 1500 bp EcoRI-to-EcoRI PGK Promoter Fragment

10 μg of pB1 was digested with PvuI and EcoRI and run on a 6 percent acrylamide gel. The 1.3 kb PvuI-to-EcoRI DNA band from the PGK 5'-flanking DNA was isolated by electroelution. 10 μg of pPGK-300 was digested with EcoRI and PvuI and the 312 bp promoter fragment was isolated by electroelution after electrophoresing the digestion mix on a 6 percent gel. 5 μg of pFRL4 was cut with EcoRI, ethanol precipitated then treated with bacterial alkaline phosphatase at 68⁻ for 45 minutes. After 3 X phenol/chloroform treating the DNA, ethanol precipitation, and resuspension in 20 ml of dIH2O; 200 ng of the vector was ligated with 100 ng of 312 bp EcoRI-to-PvuI DNA from pPGK-300 and 100 ng of EcoRI-to-PvuI DNA from pB1. The ligation mix was used to transform E. coli strain 294 to ampicillin resistence. From one of the Ap$^R$ colonies was obtained pPGK-1500. This plasmid contains the 1500 bp PGK promoter fragment as an EcoRI-to-EcoRI or HindIII-to-EcoRI piece of DNA.

Construction of expression vector (FIG. 6)

20 μg of pFRL4 was digested with HindIII and BglII then electrophoresed in a 6 percent acrylamide gel. The 230 bp fragment from the TRP1 gene containing part of the structural gene and the 3' untranslated region (28) was isolated by electroelution from the gel slice. This is the yeast terminator restriction fragment.

10 μg of pHS94 was restricted with HindIII and EcoRI, run on a 6 percent acrylamide gel. The 870 bp band representing the HBsAg gene was isolated by electroelution.

3 μg of the HbsAg gene was ligated with 1 μg of the TRP1 "terminator" for 2 hours at room temperature. This solution was then restricted with EcoRI and BglII and electrophoresed on a 6 percent acrylamide gel. The 1.1 kb band corresponding to 5'-HBsAg/TRP-3' DNA fragment was isolated by electroelution. 50 μg of pPGK-1500 was restricted with HindIII and EcoRI then electrophoresed on a 6 percent acrylamide gel. The 1.5 kbp PGK promoter fragment was isolated by electroelution. 10 μg of pCV13 was restricted with HindIII and BamHI then electrophoresed on a 1 percent agarose gel. The large vector fragment was isolated by electroelution. 0.9 μg of pCV13 (HindII to BamHI), 150 ng of HindIII to EcoRI PGK promoter fragment, and 100 ng of EcoRI to BglII HbsAg/TRP1 fusion were ligated for 12 hours at 16° C. and then used to transform *E. coli* strain 294 to ampicillin resistence. Miniscreen analysis of a number of transformants indicated that some colonies contained the proper vector construction with promoter-HBsAg structural gene-TRP1 terminator. Several of these plasmids were used to transform yeast to Leu+.

Transformation of yeast and assay for HbsAg

Yeast strain XV610-8C (deposited under accession number 20622 in the American Type Culture Collection, 12301 Parklawn Dr., Rockville, MD 20852, USA) was grown in YPD (29), prepared for transformation using standard procedures (20, 21), and transformed to leucine prototrophy(Leu+) using plasmid pCV13 or pYeHBs on minimal YNB(-leu) (See Strains and Media). Transformant colonies were prepared for HBsAg radioimmune assay (Abbott Labs) as follows:
  (1) Grow 10 mls of yeast in YNB-leucine at 30° C. with aeration to an absorbance at 660 mμ of 1.0.
  (2) Spin culture 5 min at 5000 xg. Discard supernatant.
  (3) Resuspend cells in 500 μl of PBS (20 mM sodium phosphate at pH=7 plus 0.14 m NaCl), add 1.5 gram sterile glass beads (0.45–0.50 mm) and vortex 5 min (keeping cold by putting on ice intermittantly).
  (4) Spin cell extract 5,000 kg for 3 min at 4° C. Use 200 μl of cell exctact for standard radioimmune assay. Cell extract was diluted using PBS.

Evidence for HBsAg Expression in Yeast by pYeHBs pYeHBs and pCV13 were used to transform yeast strain XV610-8C to leucine prototropy in YNB-leu minimal media. The presence of the plasmid was verified by growing these yeast on plates with no luecine selection (YPD) to colonies followed by replicaplating to YNB(-leucine) plates (2 percent agar). Fifty to 60 percent of the colonies that grew on YEPD grew on YNB-leu demonstrating that 50–60 percent of yeast contained pCV13 or pYeHBs. It should be noted that a Leu+ revertant would show growth of all colonies on YNB-leu. PCV13 stability in the yeast was no greater than pYeHBs, suggesting that the production of HBsAg (as discussed infra.) does not put pressure on cells to restrict copy number.

Transformant yeast were grown in liquid leucine selection media (YNB-leu) then broken open by vortexing with a glass bead suspension (infra.). A radioimmune assay was used to assess HBsAg production in the cleared yeast extract. The 22 nm HBsAg particle is roughly 1000 times more antigenic than the HBsAg monomers alone and we used antibody prepared against this particle. The RIA on the yeast extract indicates the production of HBsAg from pYeHBs in yeast. [pCV13 transformed yeast extracts produce no HBsAg antigen material.]

Characterization of HBsAg in Yeast (1) 200 μl of yeast extract prepared as described above was layered on top of a 5 ml linear density gradient consisting of 5–20 percent sucrose (w/v) in 20 mM tris-HCl (pH 7.4), 0.5 mM EDTA, and 0.5 M NaCl then centrifuged in a SW50.1 rotor at 45,000 rpm for 2 hours. Fractions were collected and assayed for HBsAg by radioimmune assay.

(2) 200 μl of extract from the same source as above was layered on top of a 5 ml solution containing 20 mM Tris-HCl (pH 7.4), 0.5 mM EDTA, and CsCl (density 1.2 g/cc) then centrifuged in a SW50.1 rotor at 45,000 rpm for 70 hours. HBsAg was assayed as described above and the density of CsCl was determined by recording the refractive index of each gradient fraction.

Figure 7:
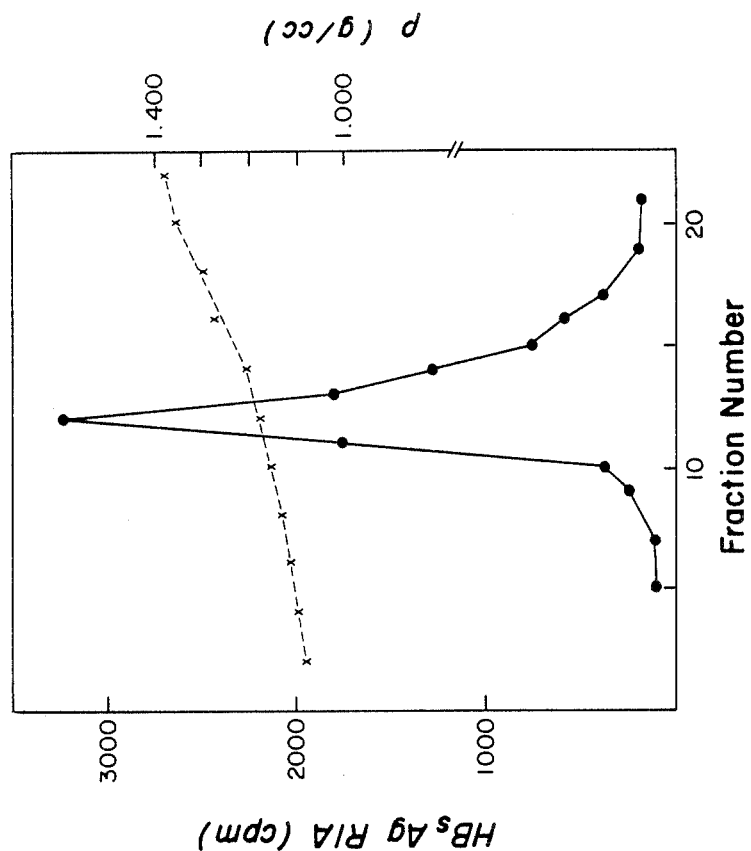
FIG. 7 depicts: (A) sucrose gradient sedimentation of yeast produced HBsaG compared with 22 nm particle and (B) a corresponding CsCl gradient centrifugation thereof.
Figure 7:
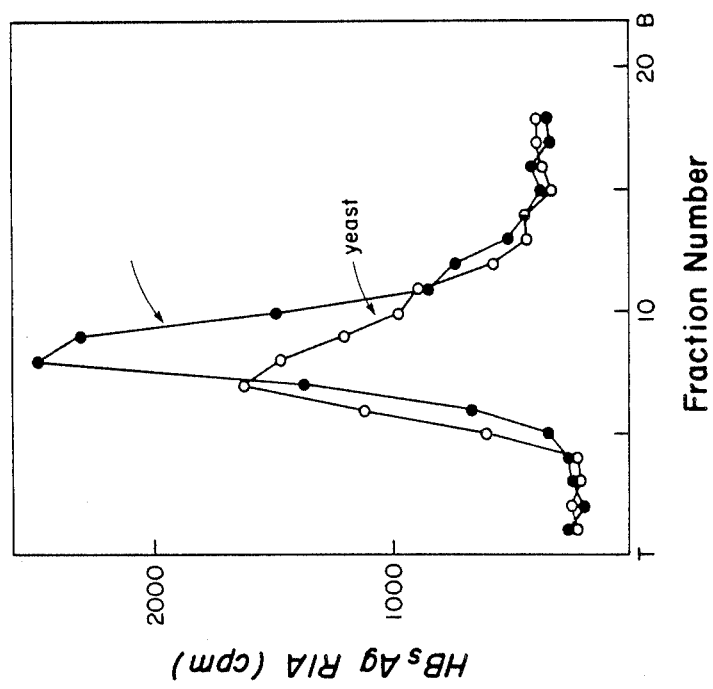
Figure 8:
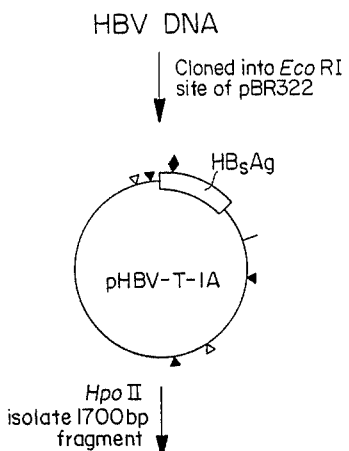
FIG. 8 depicts the construction of plasmid pSVR containing SV40 DNA with a deletion of the coding region for the VP-1 protein.
Figure 8:
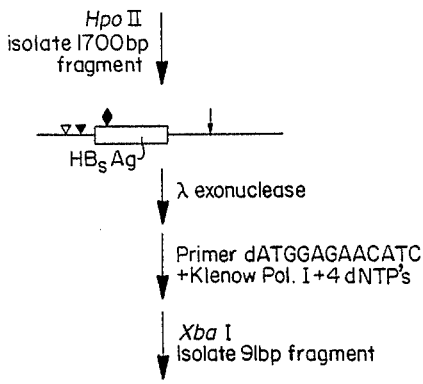
Figure 8:
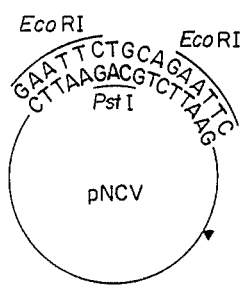
Figure 8:
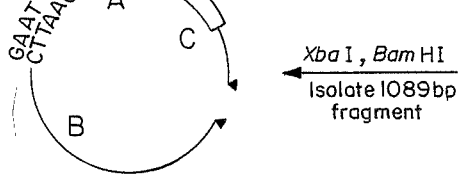
Figure 8:
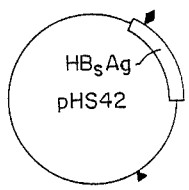
Figure 8:
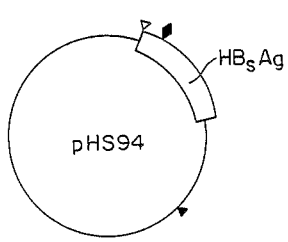

Hepatitis surface antigen is synthesized and secreted from liver cells as a particle (22 nm particle). In the construction described above, only the coding region representing the mature structural gene plus some 3' untranslated sequences were included. We assessed the particulate nature of the hepatitis surface antigen monomer within the yeast cell. To this end, aliquots of a yeast cell extract containing HBsAg were subjected to sedimentation velocity and sedimentation equilibrium analysis. As shown in FIG. 7, the hepatitis surface antigen synthesized in yeast cell has a sedimentation rate that is virtually identical to that of the "22 nm particle" form of HBsAg obtained from a cell line (PLCWIII) secreting authentic 22 nm particles.

HBsAg synthesized in yeast has a buoyant density of 1.18 g/cm$^3$ as determined by sedimentation equilibrium analysis. This value is slightly lower than that of HBsAG synthesized in the infected liver cell.

VACCINE PREPARATION

The vaccines of the present invention, incorporating the HBsAg produced as herein described, can be prepared according to known methods, wherein said HBsAg is combined in admixture with a suitable vehicle. Suitable vehicles include, for example, saline solutions, various known adjuvants, or other additives recognized in the art for use in compositions applied to prevent viral infections. Such vaccines will contain an effective amount of the HBsAg hereof and a suitable amount of vehicle in order to prepare a vaccine useful for effective administration to the host. Attention is also directed to *New Trends and Developments in Vaccines*, Editors: A. Voller and H. Friedman, University Park Press, Baltimore, 1978, which is hereby incorporated by reference, for further background details on the preparation of vaccines.

Bibliography

1. Broach, J. R., Strathern, J. N., and Hicks, J. B. *Gene* 8, 121–133 (1979).
2. Ratzkin, B., and Carbon, J. *Proc. Natl. Acad. Sci. U.S.A.* 74, 487–491 (1977).
3. Chinault, A. C., and Carbon, J. *Gene* 5 111–126 (1979).
4. Hinnen, A., Hicks, J. D., and Fink, G. R. *Proc. Natl. Acad. Sci.* U.S.A. 75, 1929–1933 (1978).
5. Hitzeman, R. A., Clarke, L., and Carbon, J. *J. Biol. Chem.* 255, 12073 (1980).
6. Hess, B., Boiteux, A., and Kruger, J. *Adv. Enzyme Regul.* 7, 149–167 (1968).

7. Holland, J. J., and Holland, J. P. *Biochemistry* 17, 4900–4907 (1978).
8. Bostian, K. A., Lemire, J. M., Cannon, L. E., and Halvorson, H. O. *Proc. Natl. Acad. Sci. U.S.A.* 77, 4504–4508 (1980).
9. Abstracts of papers presented at the 1981 meeting on *The Molecular Biology of Yeast* (Aug. 11–Aug. 16, 1981) Cold Spring Harbor Laboratory, Cold Spring Harbor, New York.
10. Chambon, P. *Ann. Rev. Biochem.* 44, 613–638 (1975).
11. Goeddel, D. V., Shepard, H. M., Yelverton, E., Leung, D., and Crea, R. *Nucleic Acids Research* 8, 4057–4073 (1980).
12. No reference.
13. Goeddel, D. V. et. al. *Nature* 287 411–416 (1980).
14. P. Valenzuela, et. al. *Nature*, 280, 815–819. (1979).
15. P. Charnay et. al. *Proc. Natl. Acad. Sci. (U.S.A.)* 76, 2222–2226 (1979).
16. H. Jacobsen et. al. *Eur. J. Biochem.* 45, 623. (1974).
17. Clarke, L., and Carbon, J. *Cell* 9, 91–99 (1976).
18. Davis, R. W., Thomas, M. Cameron, J., St. John, T. P., Scherer, S., and Padgett, R. A. *Methods in Enzymology* 65, 404–411.
19. Clark, L., and Carbon, J. *Proc. Natl. Acad. Sci. U.S.A.* 72, 4361–4365 (1975).
20. Beggs, J. D. *Nature* 275, 104–109 (1978).
21. Hinnen, A., Hicks, J. B., and Fink, G. R. *Proc. Natl. Acad. Sci. U.S.A.* 75, 1929–1933 (1978).
22. Birnboim, H. C., and Poly, J. *Nucleic Acids Res.* 7, 1513–1523.
23. Bachman, K., Ptashne, M., and Gilbert, W. *Proc. Natl. Acad. Sci. U.S.A.* 73, 4174–4178 (1976).
24. Miller, J. H. *Experiments in Molecular Genetics*, pp. 431–433, Cold Spring Harbor Laboratory, Cold Spring Harbor, N.Y.
25. Maxam, A. M., and Gilbert, W. *Methods in Enzymol.* 65, 490–565 (1980).
26. Crea, R. and Horn, T. *Nucleic Acids Res.* 8, 2331–2348 (1980).
27. Bolviar, F., Rodriguez, R. L. Green, P. Y., Betlach, M. C., Heyneker, H. L., Boyer, H. W., Crosa, Y. H., and Falkow, S. *Gene* 2, 95–113 (1977).
28. Tschumper, G., and Carbon J. *Gene* 10, 157–166 (1980).
29. Laboratory Manual for a course *Methods in Yeast Genetics* Cold Spring Harbor Laboratory, Sherman, Fink, and Hicks, Cold Spring Harbor, N.Y.

We claim:

1. A DNA expression vector capable of replication and phenotypic selection in yeast host strain comprising a promoter compatible with a yeast host strain and a DNA sequence encoding hepatitis B surface antigen, said sequence being positioned together with translational start and stop signals in said vector under control of said promoter such that in a transformant yeast strain it is expressed to produce hepatitis B surface antigen in particle form having a sedimentation rate which is virtually identical to that of authentic 22 nm hepatitis surface antigen particles.

2. A yeast strain transformed with the DNA expression vector according to claim 1.

3. The yeast strain according to claim 2 obtained by transforming a leu2 auxotrophic yeast strain.

4. The yeast strain according to claim 2 obtained by transforming strain XV610-8C.

5. A fermentation culture comprising a transformed yeast according to claim 2, 3, or 4.

6. The vector of claim 1 wherein the DNA sequence encoding hepatitis B surface antigen encodes only the mature hepatitis B surface antigen structural gene.

7. A method of producing hepatitis B surface antigen in particle form suitable for use in conferring immunogenicity to hepatitis B virus in a susceptible human which comprises:

(a) providing a DNA transfer vector capable of replication and phenotypic selection in yeast host strains, (b) providing a DNA fragment comprising a promoter compatible with a yeast host strain, (c) providing a DNA fragment encoding hepatitis B surface antigen, (d) assembling the fragments of steps (a), (b) and (c) together with translational start and stop signals for the fragment of step (c) to form a replicable expression vector so that said sequence of step (c) is under control of said promoter, (e) transforming a yeast strain with the vector of step (d), (f) allowing the yeast transformant to grow under fermentation conditions until said hepatitis B surface antigen is produced therein, and (g) recovering said hepatitis B surface antigen in particle form having a sedimentation rate which is virtually identical to that of authentic 22 nm hepatitis surface antigen particles.

8. The method according to claim 7 wherein the DNA fragment of step (c) comprises, in order from the 5' end of its coding strand, a ATG translational start codon, the nucleotides encoding hepatitis B surface antigen of the hepatitis B genome, and one or more translational stop signals.

9. The method according to claim 7 wherein the yeast strain of step (e) is XV610-8C.

10. The method according to any one of claims 7 to 9 wherein the promoter of step (b) is derived from the yeast PGK promoter region.

11. The method of claim 8 wherein the start codon is the start codon for mature hepatitis B surface antigen structural gene.

* * * * *

Adverse Decisions In Interference

Patent No. 4,803,164, Ronald A. Hitzeman, Arthur D. Levinson, Daniel G. Yansura, PREPARATION OF HEPATITIS B SURFACE ANTIGEN IN YEAST, Interference No. 102,416, final judgment adverse to the patentees rendered June 30, 1999, as to claims 1-11.

*(Official Gazette July 31, 2001)*